(12) United States Patent
Jimenez et al.

(10) Patent No.: US 10,653,161 B2
(45) Date of Patent: May 19, 2020

(54) FLAVOR-ENHANCING *LACTOBACILLUS RHAMNOSUS*

(75) Inventors: Luciana Jimenez, Paris (FR); Gunnar Oeregaard, Vaerloese (DK); Jeorgos Trihaas, Oelsted (DK); Gaelle Lettier Buchhorn, Virum (DK); Ditte Marie Brandt, Valby (DK); Ditte Marie Folkenberg, Hilleroed (DK); Birgitte Vedel Thage, Graested (DK)

(73) Assignee: CHR. HANSEN A/S, Hoersholm (DK)

( * ) Notice: Subject to any disclaimer, the term of this patent is extended or adjusted under 35 U.S.C. 154(b) by 0 days.

(21) Appl. No.: 14/110,385

(22) PCT Filed: Apr. 9, 2012

(86) PCT No.: PCT/EP2012/056386
§ 371 (c)(1),
(2), (4) Date: Oct. 7, 2013

(87) PCT Pub. No.: WO2012/136832
PCT Pub. Date: Oct. 11, 2012

(65) Prior Publication Data
US 2014/0023749 A1   Jan. 23, 2014

(30) Foreign Application Priority Data

Apr. 8, 2011 (EP) .................................. 11161665

(51) Int. Cl.
*A23C 9/123* (2006.01)
*C12R 1/225* (2006.01)
(Continued)

(52) U.S. Cl.
CPC ........ *A23C 9/1234* (2013.01); *A23C 19/0323* (2013.01); *A23L 27/88* (2016.08);
(Continued)

(58) Field of Classification Search
CPC .............. A23C 9/1234; A23C 19/0323; A23C 19/0688; A23L 1/22091; A23Y 2220/73
See application file for complete search history.

(56) References Cited

U.S. PATENT DOCUMENTS 4,678,673 A   7/1987 Marshall et al.
4,867,992 A   9/1989 Boniello et al.
(Continued)

FOREIGN PATENT DOCUMENTS

EP    0 852 114 A1    7/1998
EP    1 116 1665.2    4/2011
(Continued)

OTHER PUBLICATIONS

B.D. Jyoti et al. "Diacetyl Production and growth of Lactobacillus rhamnosus on multiple substrates" 2003 World Journal of Microbiology & Biotechnology vol. 19 pp. 509-514.*

(Continued)

*Primary Examiner* — Felicia C Turner
(74) *Attorney, Agent, or Firm* — Foley & Lardner LLP

(57) ABSTRACT

The present invention relates to a composition suitable for preparing a dairy product comprising at least one starter culture and a *Lactobacillus rhamnosus* strain capable of imparting onto the dairy product and enhanced creamy flavor without affecting the rheology negatively, the fermentation time or the post-acidification of the dairy product. The present invention further relates to processes for preparing a dairy product, such as a low-fat yoghurt or cheese, which has a high content of diacetyl. A *Lactobacillus rhamnosus* strain useful for preparing such dairy product is also part of the present invention.

14 Claims, 5 Drawing Sheets

(51) Int. Cl.
| | |
|---|---|
| *A23L 27/00* | (2016.01) |
| *A23L 29/00* | (2016.01) |
| *C12N 1/20* | (2006.01) |
| *A23C 19/032* | (2006.01) |
| *C12P 7/26* | (2006.01) |
| *A23C 19/068* | (2006.01) |

(52) U.S. Cl.
CPC .............. *A23L 29/065* (2016.08); *C12N 1/20* (2013.01); *C12P 7/26* (2013.01); *C12R 1/225* (2013.01); *A23C 19/0688* (2013.01); *A23Y 2220/73* (2013.01)

(56) References Cited

U.S. PATENT DOCUMENTS

| | | | |
|---|---|---|---|
| 4,938,973 A * | 7/1990 | Klaver et al. .................. | 426/42 |
| 5,236,833 A | 8/1993 | Duboff et al. | |
| 6,410,016 B2 * | 6/2002 | Maruta et al. ............. | 424/93.45 |
| 10,226,641 B2 | 3/2019 | Hornbaek et al. | |
| 2019/0192589 A1 | 6/2019 | Hornbaek et al. | |

FOREIGN PATENT DOCUMENTS

| | | |
|---|---|---|
| EP | 2 338 250 | 6/2011 |
| WO | WO-2005/095656 A1 | 10/2005 |
| WO | WO-2011/141881 A1 | 11/2011 |

OTHER PUBLICATIONS

Jyoti et al. "Effect of preculturing conditions on growth of Lactobacillys rhamnosus on medium containing glucose and citrate" Microbiological Research 159 2004 pp. 35-42.*

Medina de Figueroa et al. Influence of tempearture of flavour compound production from citrate by L. rhamnosus ATCC 7469 Microbiological Research 155 2001 pp. 257-262.*

Valik et al. "Characterization of the growth of Lactobacillus rhamnosus GG in milk at suboptimal temperatures" Journal of Food and Nutrition Research vol. 47 No. 2 2008 pp. 60-67 [p. 60].*

Benito de Cardenas et al, "Effect of Lactate on the Growth and production of Diacetyl and Acetoin by Lactobacilli" abstract (Year: 1985).*

Gayen et al. "Elementary mode analysis to study reculturing . . . " 2007 In Silico Biology vol. 7 (Year: 2007).*

Cichosz Grayna et al. "Aroma compounds in gouda cheese produced with addition of probiotic strains", Polish Journal of Natural Sciences, vol. 21, No. 2, Jan. 1, 2006, pp. 987-997.

Database GNPD [Online] Mintel; Aug. 1, 2008 (Aug. 1, 2008), Anonymous: "Fat Free Yogurt", XP002656974, retrieved from www.gnpd.com Database accession No. 956947.

Degheidi M A et al. "Utilization of probiotic bacteria in UF white soft cheese", Egyptian Journal of Dairy Science, Egyptian Society of Dairy Science, Cairo, EG, vol. 37, No. 1, Jan. 1, 2009, pp. 73-84.

European Search Report dated Aug. 17, 2011 issued in connection with European Application No. 11161665.2.

International Preliminary Report on Patentability dated Jun. 26, 2013 issued in connection with PCT/EP2012/056386.

International Search Report dated Jun. 20, 2012 issued in connection with PCT/EP2012/056386.

Medina De Figueroa R Medina et al. "Flavour compound production and citrate metabolism in Lactobacillus rhamnosus ATCC 7469", Milchwissenschaft, VV GMBH Volkswirtschaftlicher Verlag. Munchen, DE, vol. 53, No. 11, Jan. 1, 1998, pp. 617-619.

Meilgaard M.C. et al. "Attribute Difference Tests: How does attribute X Differ Between Samples?", CRC Press article 'Sensory Evaluation Techniques', pp. 105-128, Apr. 2006.

Muhammad Ramzan et al. "Evaluation of volatile flavouring compounds in Cheddar cheese, manufactured by using Lactobacillus rhamnosus as an adjunct culture", Journal of Agroalimentary Processes and Technologies, Timisoara : Agroprint, RO , vol. 16, No. 2 Jan. 1, 2010, pp. 188-195, XP009151277, ISSN: 1453-1399 Retrieved from the Internet: URL:http://www.journal-of-agroalimentary. ro/admin/article/72109L41_Ramzan_Shan_Vol.2_01-02 2010_188-195.pdf.

Sa Xu et al. "Effect of Inoculation Level of Lactobacillus rhamnosus and Yogurt Cultures on Conjugated Linoleic Acid Content and Quality Attributes of Fermented Milk Products", Journal of Food Science, vol. 71, No. 4, May 1, 2006, pp. C275-C280.

Senel E et al. "Effect of using a biopreservative culture on some properties of set-type yoghurt", Gida, TR , vol. 31, No. 1 Jan. 1, 2006, pp. 21-26, XP009151274, ISSN: 1300-3070 Retrieved from the Internet: URL:http://www.gidadernegi.org/EN/Genel/dg.ashx? BELGEANAH=553&DIL=2&DOSYAISIM=703310103.pdf.

Jyoti et al., "Diacetyl production and growth of Lactobacillus rhamnosus on multiple substrates." World Journal of Microbiology and Biotechnology, vol. 19, pp. 509-514.

Ali, "Isolation and Identification of Lactic Acid Bacteria Isolated from Traditional Drinking Yoghurt in Khartoum State, Sudan," *Current Research in Bacteriology*, vol. 4, No. 1, pp. 16-22 (2011).

Šuškovic, et al., "Antimicrobial Activity—The Most Important Property of Probiotic and Starter Lactic Acid Bacteria," *Food Technol. Biotechnol.*, vol. 48, No. 3, pp. 296-307 (2010).

Bottari et al., "Effective identification of *Lactobacillus casei* group species: genome-based selection of the gene mutL as the target of a novel multiplex PCR assay," Microbiology, (2017) vol. 163, pp. 950-960.

De Figueroa et al., "Citrate utilization by homo- and heterofermentative lactobacilli," Microbiological Research, (2000) vol. 154, pp. 313-320.

De Figueroa et al., "Influence of temperature on flavour compound production from citrate by *Lactobacillus rhamnosus* ATCC 7469," Microbiological Research, (2001) vol. 155, pp. 257-262.

Guo et al., "Oxygen-Inducible Conversion of Lactate to Acetate in Heterofermentative *Lactobacillus brevis* ATCC 367," Applied and Environmental Microbiology, (Nov. 2017) vol. 83, Issue 21, e01659-17, pp. 1-12.

Barrette et al., "The production of mixed cultures containing strains of Lactococcus lactis, Leuconostoc cremoris and Lacobacillus rhamnosus, on commercial starter media," Journal of Industrial Microbiology and Biotechnology, vol. 25, issue 6, (2000) pp. 288-297.

Kondyli et al., "Free fatty acids and volatile compounds in low-fat Kefalograviera-type cheese made with commercial adjunct cultures," Industrial Dairy Journal, vol. 13, issue 1, (2003), pp. 47-54.

Lo et al., "The genetic basis underlying variation in production of the flavor compound diacetyl by Lactobacillus rhamnosus strains in milk," International Journal of Food Microbiology 265 (2018) 30-39.

* cited by examiner

FLAVOR-ENHANCING *LACTOBACILLUS RHAMNOSUS*

CROSS-REFERENCE TO RELATED APPLICATIONS

This application is a national phase of International Application PCT/EP2012/056386, filed Apr. 9, 2012, which was published on Oct. 11, 2012, as WO 2012/136832, which claims the benefit of EP Application No. 11161665.2, filed Apr. 8, 2011. The respective contents of each of these applications are incorporated here by reference in their entirety.

FIELD OF THE INVENTION

The present invention relates to a composition suitable for preparing a dairy product comprising at least one starter culture and a *Lactobacillus rhamnosus* strain capable of imparting onto the dairy product an enhanced creamy flavor without affecting negatively the rheology of the dairy product. The present invention further relates to processes for preparing a dairy product, such as a low-fat yoghurt or cheese, that has a high content of diacetyl. A *Lactobacillus rhamnosus* strain useful for preparing such dairy products is also part of the present invention.

BACKGROUND ART

In the dairy industry products with a low or no fat content are experiencing increasing demand from consumers.

However, such low fat dairy products often experience a lack of creamy flavor.

Diacetyl is a high value product and it is used in the dairy industry as a buttery flavor-producing compound added to such products as margarines and oil-based products.

Heterolactic acid bacteria form diacetyl/acetoin as a by-product along with lactate as the main product. The cells form active acetaldehyde from pyruvate and thiamine pyrophosphate by pyruvate oxidase. The active acetaldehyde condenses with another molecule of pyruvate and forms alpha-acetolactate synthase. Formation of diacetyl in *Lactobacillus rhamnosus* is not well understood—in *Lactococcus lactis* subsp. *lactis* biovar. diacetylactis it has been suggested that alpha-acetolactate is oxidized to diacetyl by an alpha acetolactate oxidase (Jyoti et al 2003). Acetoin is formed directly by decarboxylation of alpha-acetolactate. Acetoin formation may also occur by the irreversible diacetyl reductase of diacetyl into acetoin.

*Lactobacillus rhamnosus* is a heterolactic acid bacterium which can be used to produce flavor compounds like diacetyl and acetoin (Jyoti et al. 2003). The level of diacetyl produced depends on the strain as well as the substrate on which it is grown.

U.S. Pat. Nos. 4,867,992 and 5,236,833 relate to processes for production of diacetyl by fermenting a coffee substrate and a pectin substrate, respectively, with a lactic acid producing bacteria.

The preparation, concentration and addition of diacetyl and/or acetoin to food products are connected with substantial costs.

U.S. Pat. No. 4,678,673 is directed to oilseed products fermented with a *Lactobacillus rhamnosus* strain which produces diacetyl and acetoin. The fermented oilseed products have a buttery or dairy-like flavor. There is no mention of use of *Lactobacillus rhamnosus* in dairy products.

Thus, there exists a need for a process of preparing dairy products with improved creamy flavor without the costly addition of diacetyl and/or acetoin.

SUMMARY OF THE INVENTION

It is an object of the present invention to provide a composition and a method for preparing a dairy product improved with an enhanced creamy flavor imparted by the presence of a strain of *Lactobacillus rhamnosus*.

It is another object of the present invention to provide a novel *Lactobacillus rhamnosus* strain with improved properties in relation to being able to give an enhanced creamy flavor to a dairy product, such as a yoghurt or cheese.

Additional objects will become apparent hereinafter and still others will be obvious to one skilled in the art to which the invention pertains.

As can be seen in the working examples herein, the described *Lactobacillus rhamnosus* strain CHCC12697 that was deposited with the German Collection of Microorganisms and Cell Cultures (DSMZ) under the accession no. DSM24616 produces diacetyl and acetoin thereby giving enhanced creamy flavor to a dairy product, without significantly affecting the rheology and the post-acidification of the dairy product.

Accordingly, a first aspect of the present invention relates to a composition for preparing a dairy product comprising at least one starter culture and a *Lactobacillus rhamnosus* strain.

In a much preferred embodiment the *Lactobacillus rhamnosus* strain is a *Lactobacillus rhamnosus* CHCC12697 that was deposited with the German Collection of Microorganisms and Cell Cultures (DSMZ) under accession no. DSM24616 or a mutant strain thereof, wherein the mutant strain is obtained by using the deposited strain as starting material.

A second aspect of the present invention relates to use of a composition according to the first aspect of the present invention for preparing a dairy product.

A third aspect of the present invention is directed to a method for producing a dairy product, the method comprising the steps:

a) inoculating a milk substrate with the composition according to the first aspect of the present invention;
b) fermenting the milk substrate;
c) optionally adding further microorganisms and/or additives to the milk substrate;
d) optionally post-treating the milk substrate; and
e) optionally packaging the dairy product.

A fourth aspect of the invention relates to a dairy product obtainable by the method according to the third aspect of the invention.

A fifth aspect of the present invention relates to a *Lactobacillus rhamnosus* CHCC12697 strain that was deposited with the German Collection of Microorganisms and Cell Cultures (DSMZ) under accession no. DSM24616 or a mutant strain thereof, wherein the mutant strain is obtained by using the deposited strain as starting material.

Figure 2:
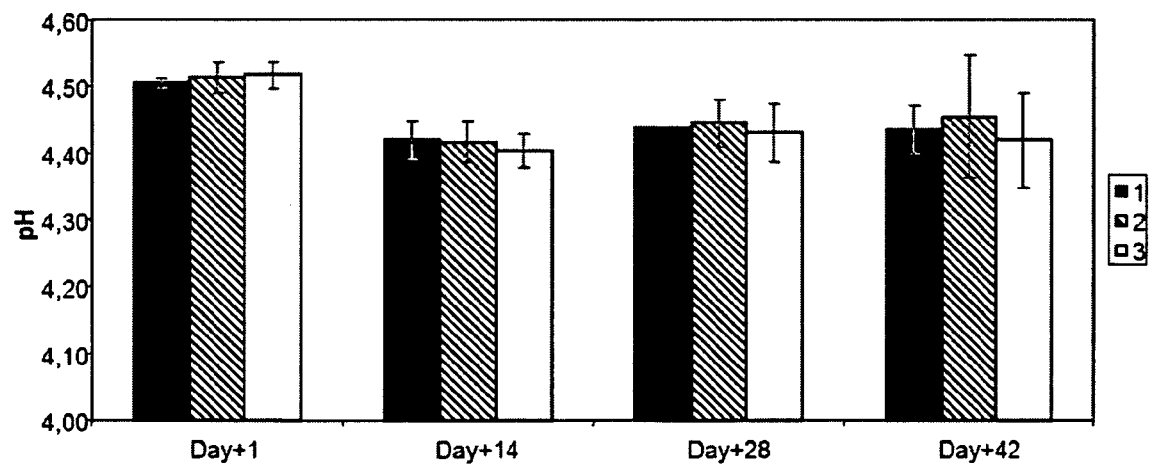

FIG. 2 illustrates evolution of the pH in yoghurt over 42 days. Yoghurts were made with a lactic acid bacteria culture containing multiple strains of *Streptococcus thermophilus* and *Lactobacillus bulgaricus* containing 0% *Lactobacillus rhamnosus* CHCC12697 (1), 7.5% *Lactobacillus rhamnosus* CHCC12697 (2), and 15% *Lactobacillus rhamnosus* CHCC12697 (3). Standard deviation values are calculated from 3 replicates.

Figure 3:
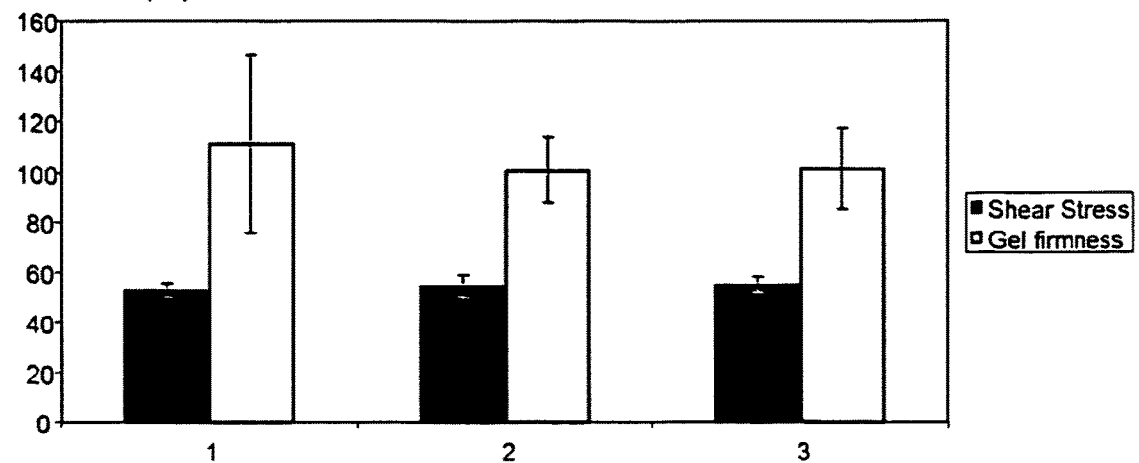

FIG. 3 depicts rheological measurements for yoghurts. Yoghurts were made with a lactic acid bacteria culture containing multiple strains of *Streptococcus thermophilus* and *Lactobacillus bulgaricus* containing 0% *Lactobacillus rhamnosus* CHCC12697 (1), 7.5% *Lactobacillus rhamnosus* CHCC12697 (2), and 15% *Lactobacillus rhamnosus* CHCC12697 (3). Standard deviation values are calculated from 3 replicates.

Figure 4:
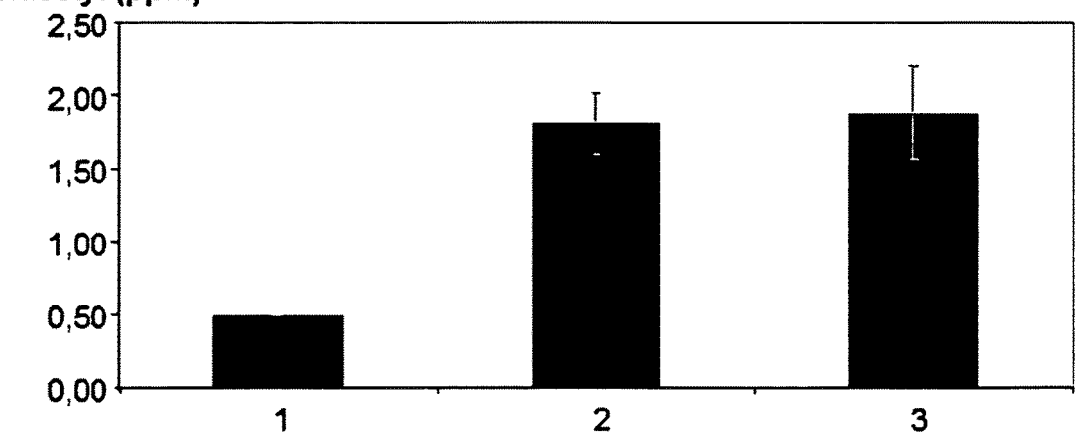

FIG. 4 shows diacetyl in yoghurts. Yoghurts were made with a lactic acid bacteria culture containing multiple strains of *Streptococcus thermophilus* and *Lactobacillus bulgaricus* containing 0% *Lactobacillus rhamnosus* CHCC12697 (1), 7.5% *Lactobacillus rhamnosus* CHCC12697 (2), and 15% *Lactobacillus rhamnosus* CHCC12697 (3). Standard deviation values are calculated from 2 replicates.

Figure 5:
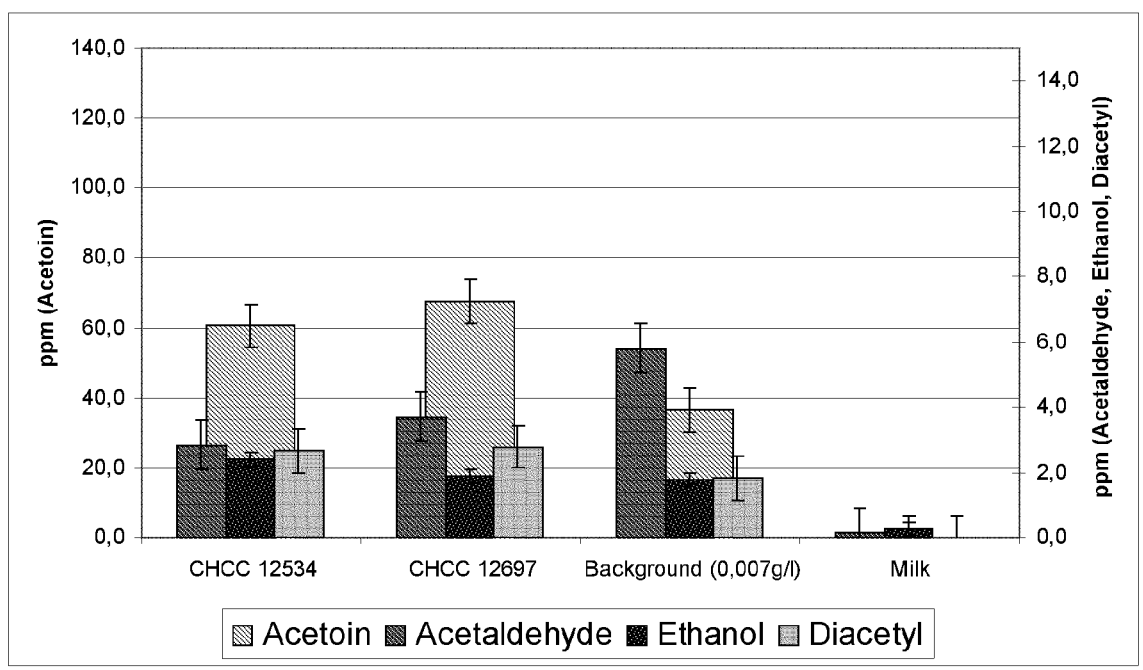

FIG. 5 shows concentrations of volatile compounds (VOC) in the fermented milk after fermentation with a single strain of *Lactobacillus rhamnosus* CHCC12534 (inoculated at 0.003 g/l) or *Lactobacillus rhamnosus* CHCC12697 (inoculated at 0.003 g/l) and of yoghurt background (*Streptococcus thermophilus* and *Lactobacillus bulgaricus* (inoculated at a total of 0.007 g/l)) at 43° C. in milk.

Figure 6:
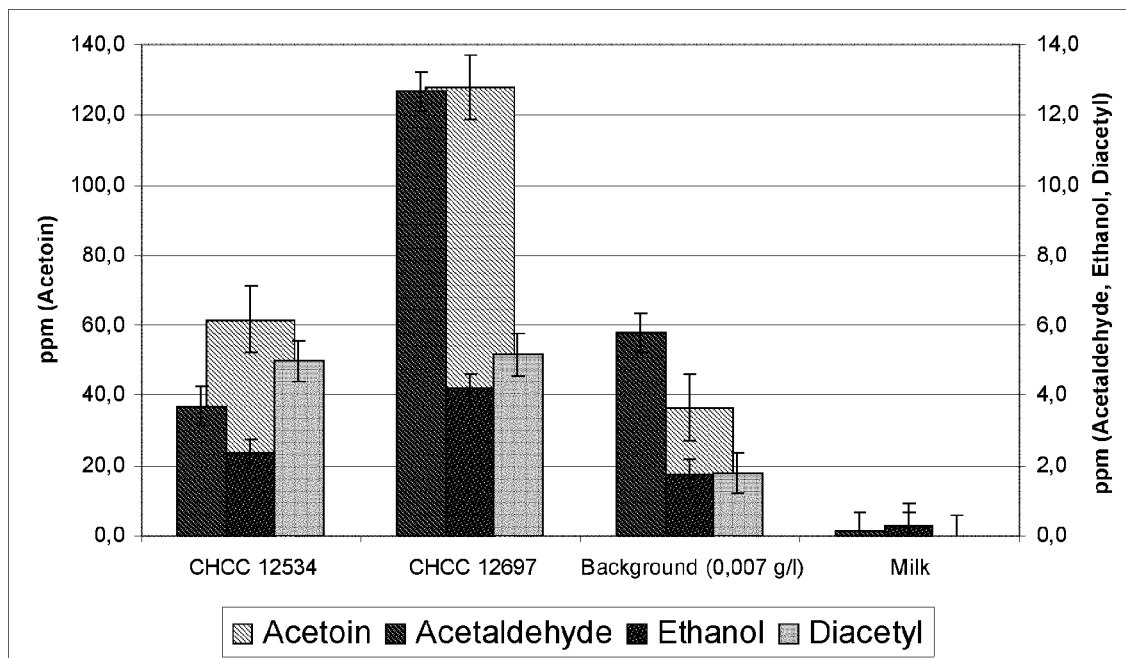

FIG. 6 shows concentrations of volatile compounds (VOC) in the fermented milk after fermentation with strains *Lactobacillus rhamnosus* CHCC12534 (inoculated at 0.003 g/l) or *Lactobacillus rhamnosus* CHCC12697 (inoculated at 0.003 g/l) in yoghurt background (*Streptococcus thermophilus* and *Lactobacillus bulgaricus* (inoculated at a total of 0.007 g/l)) at 43° C. in milk.

Figure 7:
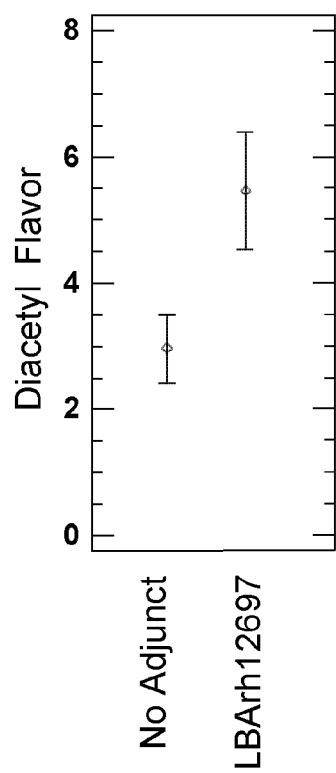

FIG. 7 shows sensory evaluation of diacetyl flavor in Gouda40+ cheese with (LBArh12697) or without (No Adjunct) addition of *Lactobacillus rhamnosus* CHCC12697 (inoculated at 0.02 (w/w)) after 7 weeks of ripening. Results were presented as mean sensory value with 95.0 percent Least Significant Distance intervals.

Figure 8:
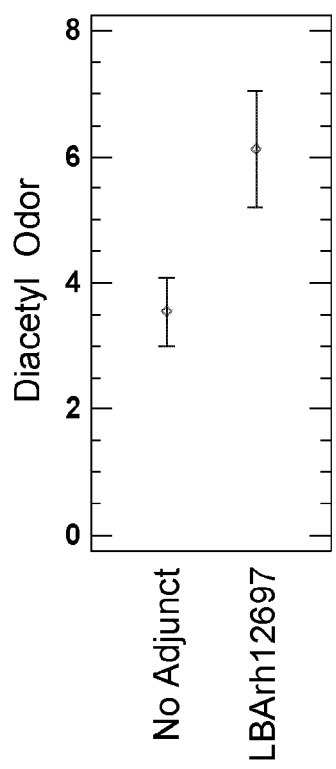

FIG. 8 shows sensory evaluation of diacetyl odor in Gouda40+ cheese with (LBArh12697) or without (No Adjunct) addition of *Lactobacillus rhamnosus* CHCC12697 (inoculated at 0.02% (w/w)) after 7 weeks of ripening. Results were presented as mean sensory value with 95.0 percent Least Significant Distance intervals.

Figure 9:
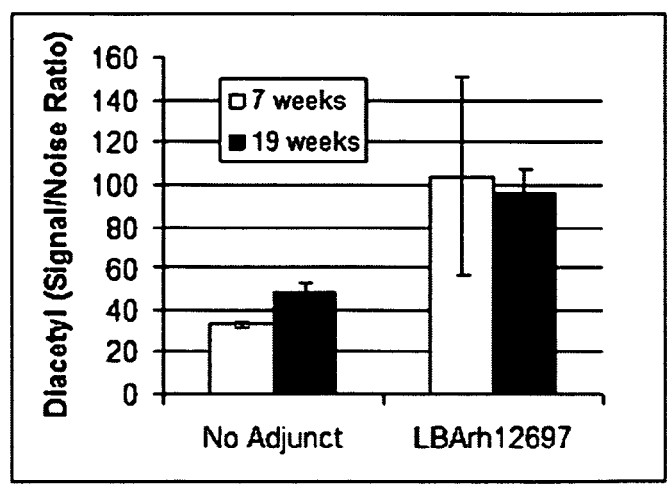

FIG. 9 shows amount of diacetyl detected in Gouda40+ cheese with (LBArh12697) or without (No Adjunct) addition of *Lactobacillus rhamnosus* CHCC12697 (inoculated at 0.02% (w/w)) after 7 and 19 weeks of ripening, respectively. Results were presented as mean diacetyl value (Signal/Noise ratio) with standard deviation intervals.

DETAILED DESCRIPTION OF THE INVENTION

Definitions

As used herein, the term "lactic acid bacterium" designates a gram-positive, microaerophilic or anaerobic bacterium, which ferments sugars with the production of acids including lactic acid as the predominantly produced acid, acetic acid and propionic acid. The industrially most useful lactic acid bacteria are found within the order "Lactobacillales" which includes *Lactococcus* spp., *Streptococcus* spp., *Lactobacillus* spp., *Leuconostoc* spp., *Pseudoleuconostoc* spp., *Pediococcus* spp., *Brevibacterium* spp., *Enterococcus* spp. and *Propionibacterium* spp. Additionally, lactic acid producing bacteria belonging to the group of the strict anaerobic bacteria, bifidobacteria, i.e. *Bifidobacterium* spp., are generally included in the group of lactic acid bacteria. These are frequently used as food cultures alone or in combination with other lactic acid bacteria.

Lactic acid bacteria, including bacteria of the species *Lactobacillus* spp. and *Streptococcus thermophilus*, are normally supplied to the dairy industry either as frozen or freeze-dried cultures for bulk starter propagation or as so-called "Direct Vat Set" (DVS) cultures, intended for direct inoculation into a fermentation vessel or vat for the production of a dairy product, such as a fermented milk product or a cheese. Such lactic acid bacterial cultures are in general referred to as "starter cultures" or "starters".

The term "mesophile" herein refers to microorganisms that thrive best at moderate temperatures (15° C.-40° C.). The industrially most useful mesophilic bacteria include *Lactococcus* spp. and *Leuconostoc* spp. The term "mesophilic fermentation" herein refers to fermentation at a temperature between about 12° C. and about 35° C. The term "mesophilic dairy product" refers to dairy products prepared by mesophilic fermentation of a mesophilic starter culture and include such dairy products as buttermilk, sour milk, cultured milk, smetana, sour cream and fresh cheese, such as quark, tvarog and cream cheese.

The term "thermophile" herein refers to microorganisms that thrive best at temperatures above 43° C. The industrially most useful thermophilic bacteria include *Streptococcus* spp. and *Lactobacillus* spp. The term "thermophilic fermentation" herein refers to fermentation at a temperature above about 35° C. The term "thermophilic dairy product" refers to dairy products prepared by thermophilic fermentation of a thermophilic starter culture and include such dairy products as yoghurt.

The term "milk" is to be understood as the lacteal secretion obtained by milking any mammal, such as cows, sheep, goats, buffaloes or camels. In a preferred embodiment, the milk is cow's milk. The term milk also includes protein/fat solutions made of plant materials, e.g. soy milk.

The term "milk substrate" may be any raw and/or processed milk material that can be subjected to fermentation according to the method of the invention. Thus, useful milk substrates include, but are not limited to, solutions/suspensions of any milk or milk-like products comprising protein, such as whole or low fat milk, skim milk, buttermilk, reconstituted milk powder, condensed milk, dried milk, whey, whey permeate, lactose, mother liquid from crystallization of lactose, whey protein concentrate, or cream. Obviously, the milk substrate may originate from any mammal, e.g. being substantially pure mammalian milk, or reconstituted milk powder.

Prior to fermentation, the milk substrate may be homogenized and pasteurized according to methods known in the art.

"Homogenizing" as used herein means intensive mixing to obtain a soluble suspension or emulsion. If homogenization is performed prior to fermentation, it may be performed so as to break up the milk fat into smaller sizes so that it no longer separates from the milk. This may be accomplished by forcing the milk at high pressure through small orifices.

"Pasteurizing" as used herein means treatment of the milk substrate to reduce or eliminate the presence of live organisms, such as microorganisms. Preferably, pasteurization is attained by maintaining a specified temperature for a specified period of time. The specified temperature is usually attained by heating. The temperature and duration may be selected in order to kill or inactivate certain bacteria, such as harmful bacteria. A rapid cooling step may follow.

"Fermentation" in the methods of the present invention means the conversion of carbohydrates into alcohols or acids through the action of a microorganism. Preferably, fermentation in the methods of the invention comprises conversion of lactose to lactic acid.

Fermentation processes to be used in production of dairy products are well known and the person of skill in the art will know how to select suitable process conditions, such as temperature, oxygen, amount and characteristics of microorganism(s) and process time. Obviously, fermentation conditions are selected so as to support the achievement of the present invention, i.e. to obtain a dairy product in solid (such as a cheese) or liquid form (such as a fermented milk product).

In the present context, the term "shear stress" determines viscosity. Viscosity (unit is Pa s) is defined as Shear Stress (Pa)/Shear rate (1/s).

Shear stress value is reported as a standard herein at shear rate=300 1/s. Sensory experiments have shown (data not shown) that the best correlation between rheological measurements and sensory viscosity/mouth thickness are found when using the viscosity measured at shear rate 300 1/s.

In the present context, the term "mutant" should be understood as a strain derived from a strain of the invention by means of e.g. genetic engineering, radiation, UV light, and/or chemical treatment and/or methods that induce changes in the genome. It is preferred that the mutant is a functionally equivalent mutant, e.g. a mutant that has substantially the same, or improved, properties (e.g. regarding diacetyl production, viscosity, gel stiffness, mouth coating, flavor, post acidification, acidification speed, and/or phage robustness) as the mother strain. Such a mutant is a part of the present invention. Especially, the term "mutant" refers to a strain obtained by subjecting a strain of the invention to any conventionally used mutagenization treatment including treatment with a chemical mutagen such as ethane methane sulphonate (EMS) or N-methyl-N'-nitro-N-nitroguanidine (NTG), UV light or to a spontaneously occurring mutant. A mutant may have been subjected to several mutagenization treatments (a single treatment should be understood as containing one mutagenization step followed by a screening/selection step), but it is presently preferred that no more than 20, or no more than 10, or no more than 5, treatments (or screening/selection steps) are carried out. In a presently preferred mutant, less that 5%, or less than 1% or even less than 0.1% of the nucleotides in the bacterial genome have been shifted with another nucleotide, or deleted, compared to the mother strain.

The use of the terms "a" and "an" and "the" and similar references in the context of describing the invention (especially in the context of the following claims) are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Implementation and Aspects of the Invention

The inventors of the present invention have surprisingly discovered that by inoculating and fermenting a milk substrate with a strain of *Lactobacillus rhamnosus* in addition to a starter culture it is possible to impart onto the resulting dairy product a pleasant creamy flavor without negatively affecting the texture of the dairy product, the fermentation time and post-acidification.

The enhanced creamy flavor was detected in dairy products prepared both by mesophilic (26° C. and 30° C.) and thermophilic (43° C.) fermentation processes in the presence of a *Lactobacillus rhamnosus* CHCC12697 that was deposited with the German Collection of Microorganisms and Cell Cultures (DSMZ) under accession no. DSM24616.

By the term "enhanced creamy flavor" is meant that the content of diacetyl and/or acetoin in the product is increased and/or that the creamy flavor of the product as determined by a sensory panel is enhanced compared to a product which does not comprise a *Lactobacillus rhamnosus* strain according to the present invention.

Without wishing to be bound by theory, it is thought that the enhanced creamy flavor imparted to the dairy product by a *Lactobacillus rhamnosus* strain according to the present invention is due to the enhanced production of diacetyl and/or acetoin by the *Lactobacillus rhamnosus* strain.

The dairy product in a preferred embodiment is a low/no fat fermented milk product or cheese which essentially lacks a creamy flavor when a *Lactobacillus rhamnosus* strain according to the present invention has not been used in the fermentation or has not been used in the fermentation.

The *Lactobacillus rhamnosus* strain as described herein is useful in a composition for the preparation of a dairy product comprising at least one starter culture and the *Lactobacillus rhamnosus* strain.

Typically, such a composition comprises the bacteria in a concentrated form including frozen, dried or freeze-dried concentrates typically having a concentration of viable cells, which is in the range of $10^4$ to $10^{12}$ cfu (colony forming units) per gram of the composition including at least $10^4$ cfu per gram of the composition, such as at least $10^5$ cfu/g, e.g. at least $10^6$ cfu/g, such as at least $10^7$ cfu/g, e.g. at least $10^8$ cfu/g, such as at least $10^9$ cfu/g, e.g. at least $10^{10}$ cfu/g, such as at least $10^{11}$ cfu/g. Thus, the antimicrobial composition of the invention is preferably present in a frozen, dried or freeze-dried form, e.g. as a Direct Vat Set (DVS) culture. However, as used herein the antimicrobial composition may also be a liquid that is obtained after suspension of the frozen, dried or freeze-dried cell concentrates in a liquid medium such as water or PBS buffer. Where the antimicrobial composition of the invention is a suspension, the concentration of viable cells is in the range of $10^4$ to $10^{12}$ cfu (colony forming units) per ml of the composition including at least $10^4$ cfu per ml of the composition, such as at least $10^5$ cfu/ml, e.g. at least $10^6$ cfu/ml, such as at least $10^7$ cfu/ml, e.g. at least $10^8$ cfu/ml, such as at least $10^9$ cfu/ml, e.g. at least $10^{10}$ cfu/ml, such as at least $10^{11}$ cfu/ml.

The composition may additionally contain as further components cryoprotectants and/or conventional additives including nutrients such as yeast extracts, sugars and vitamins, e.g. vitamin A, C, D, K or vitamins of the vitamin B family. Suitable cryoprotectants that may be added to the compositions of the invention are components that improve the cold tolerance of the microorganisms, such as mannitol, sorbitol, sodium tripolyphosphate, xylitol, glycerol, raffinose, maltodextrin, erythritol, threitol, trehalose, glucose and fructose. Other additives to may include, e.g., carbohydrates, flavors, minerals, enzymes (e.g. rennet, lactase and/or phospholipase).

As it is normal in lactic acid bacterial fermentation processes to apply a mixed culture as a starter culture, the composition will in certain embodiments comprise a multiplicity of strains either belonging to the same species or belonging to different species. A typical example of such a useful combination of lactic acid bacteria in a starter culture is a mixture of a *Lactobacillus bulgaricus* strain and a *Streptococcus thermophilus* strain.

In a preferred embodiment of the present invention the starter culture is a thermophilic starter culture and the composition is suitable for thermophilic fermentation.

In another preferred embodiment the starter culture is selected from the group consisting of the genera *Streptococcus* and *Lactobacillus*. The starter culture in a preferred embodiment comprises at least one *Lactococcus lactis* strain. The starter culture may comprise any *Lactococcus lactis* strain known in the art, such as strains from the *Lactococcus lactis* subsp. *cremoris, Lactococcus lactis* subsp. *hordniae* or *Lactococcus lactis* subsp. *lactis*. In yet another preferred embodiment the starter culture comprises a *Lactococcus lactis* subsp. *cremoris* strain and a *Lactococcus lactis* subsp. *lactis* strain.

The composition can be used for preparing a dairy product with enhanced creamy flavor.

In a preferred embodiment the dairy product is a fermented milk product, such as yoghurt. In another preferred embodiment the dairy product is a cheese.

In a preferred embodiment the dairy product contains at least 0.75 ppm of diacetyl, such as at least 1.0 ppm of diacetyl, such as at least 1.5 ppm of diacetyl. The mesophilic dairy product may contain between about 0.75 ppm and 3.00 ppm of diacetyl, more preferably between about 1.00 and 2.50 ppm of diacetyl and most preferably between about 1.5 ppm and 2 ppm of diacetyl. In a preferred embodiment the mesophilic dairy product contains more than 1.5 ppm of diacetyl. The skilled person will be aware of numerous methods to determine the content of diacetyl in the dairy products of the invention. For example, the content may be determined by suitable chromatographic methods, such as static head space gas chromatography (HSGC).

As said above, an aspect of the invention relates to a method of manufacturing a dairy product with a creamy flavor comprising:
 a) inoculating a milk substrate with the composition according to the first aspect of the invention;
 b) fermenting the milk substrate;
 c) optionally adding further microorganisms and/or additives to the milk substrate;
 d) optionally post-treating the milk substrate; and
 e) optionally packaging the dairy product.

As described above, the milk substrate to be used in step a) may be any raw and/or processed milk material that can be subjected to fermentation according to the method of the invention.

The milk substrate may be inoculated with the above composition by any suitable method. For example, the milk substrate may be inoculated by direct inoculation into a fermentation vessel.

In one preferred embodiment step b) comprises fermenting the milk substrate at a temperature above about 37° C. The fermentation will preferably be carried out at a temperature of between about 38° C. to about 45° C., more preferably between about 39° C. to about 42° C. In another preferred embodiment, the milk substrate will be fermented at about 40° C. Fermentation processes to be used in production of dairy products are well known and the person of skill in the art will know how to select suitable process conditions, such as temperature, oxygen, amount and characteristics of microorganism(s) and process time. Obviously, fermentation conditions are selected so as to obtain a fermented milk product suitable in the production of a dairy product with improved flavor and high texture.

Further microorganisms and/or additives may be added to the milk substrate before, during or after fermentation of the milk substrate in step (b). Microorganisms that may be added to the milk substrates will contribute in an advantageous manner to the properties of the dairy product. For example, the microorganism may improve or support the diacetyl production, the viscosity, gel stiffness, mouth coating, flavor, post acidification, and/or acidification speed in the dairy product. Optionally, other ingredients may be added to the milk substrate, such as colors, stabilizers, e.g., pectin, starch, modified starch, CMC, etc.; or polyunsaturated fatty acids, e.g. omega-3 fatty acids. Such ingredients may be added at any point during the production process, e.g. before or after fermentation.

The milk substrate may further be post-treated by any means necessary to create the desired dairy product. For example, further components, such as cryoprotectants and/or conventional additives including nutrients such as yeast extracts, sugars and vitamins, may be added to the milk substrate. Further, the milk substrate may e.g. be homogenized or treated with heat, i.e. pasteurized.

The dairy product may be packaged in any suitable manner known in the art. For example, the dairy product may be packaged in a sealed container having a volume in the range of e.g. 25 to 1500 ml. The product may be packaged at any point during the production process, e.g. packaged next to the inoculating step and then fermented in the package.

The dairy products, which are obtained by the method, include as typical examples products such as yoghurt, sour cream, cheese and buttermilk.

A dairy product obtainable by the method above is also part of the present invention.

In a preferred embodiment the dairy product is a fermented milk product. Preferably, the fermented milk product is a yoghurt.

In yet another preferred embodiment the dairy product is a cheese.

In a preferred embodiment the dairy product contains at least 0.75 ppm of diacetyl, such as at least 1.0 ppm of diacetyl, such as at least 1.5 ppm of diacetyl.

The fifth aspect of the invention relates to the *Lactobacillus rhamnosus* CHCC12697 strain that was deposited with the German Collection of Microorganisms and Cell Cultures (DSMZ) under the accession no. DSM24616. Apart from this strain, the invention also pertains to mutants that have been derived from it, i.e. they have been obtained by using the deposited strain CHCC12697 as a starting material. The mutant strain may be derived from CHCC12697, e.g., by means of genetic engineering, radiation, UV light, chemical treatment and/or methods that induce changes in the genome. A mutant according to the invention will essentially have the same characteristics as the mother strain in terms of the production levels of acetate, acetaldehyde, diacetyl and/or acetoin. It is preferred that the mutant produces essentially at least 80% or more, at least 90% or more, at least 95% or more, or even up to 100% or more of acetate, acetaldehyde, diacetyl and/or acetoin compared with its mother strain.

It is clear for the skilled person that by using the deposited strain as starting material, the skilled reader can by conventional mutagenesis or re-isolation techniques routinely obtain further mutants or derivatives thereof that retain the herein described relevant features and advantages. Accordingly, the term "a mutant thereof" of the first aspect relates to mutant strains obtained by using the deposited strain as starting material.

Embodiments of the present invention are described below, by way of non-limiting examples.

EXAMPLES

Example 1: Screening for Thermophilic *Lactobacillus* spp. with High Acetoin Levels in Acidified Boiled-Milk A selection of 176 *Lactobacillus* sp. strains was examined for ability to acidify boiled-milk at 30° C., 37° C., 40° C. and 43° C. for approximately 24 hours. The acidified boiled milk from 37° C. incubations were examined directly after fermentation for volatile organic compounds (VOC) by means of head space gas chromatography as described in Example 5. A strain, named CHCC12697, was found to produce high levels of acetoin (135 ppm) and also fairly high levels of acetaldehyde (8 ppm) (data not shown). This strain was observed to acidify boiled-milk at both a mesophilic temperature (30-37° C.) as well as at thermophilic temperatures (40-43° C.). The strain was also observed to grow to high OD in MRS broth supplemented with 2% glucose or 2% lactose or 2% fructose or 2% galactose at 40 and 43° C. The strain was not resistant to antibiotics. Partial 16S rRNA gene sequencing showed that the strain was a *Lactobacillus rhamnosus*.

Example 2: Method for Yoghurt Make

Skim milk (DanMaelk, Arla) was fortified with 2% skim milk powder (Arta) and heat treated for 20 minutes at 90° C. This solution was inoculated with a background starter culture and with or not the *Lactobacillus rhamnosus* CHCC12697 strain.

The background starter culture used to make the yoghurt was composed of multiple strains of *Streptococcus thermophilus* and *Lactobacillus bulgaricus* in frozen Direct Vat Set (F-DVS) form inoculated at a rate of 0.02%. The *Lactobacillus rhamnosus* strain, in F-DVS form, was added to the background starter culture in the amounts described in the result section. At inoculation, cell counts were above $1 \times 10^{10}$ cfu/g for the *Streptococcus thermophilus* and *Lactobacillus rhamnosus* strains and above $1 \times 10^8$ cfu/g for the *Lactobacillus bulgaricus* strains.

Figure 1:
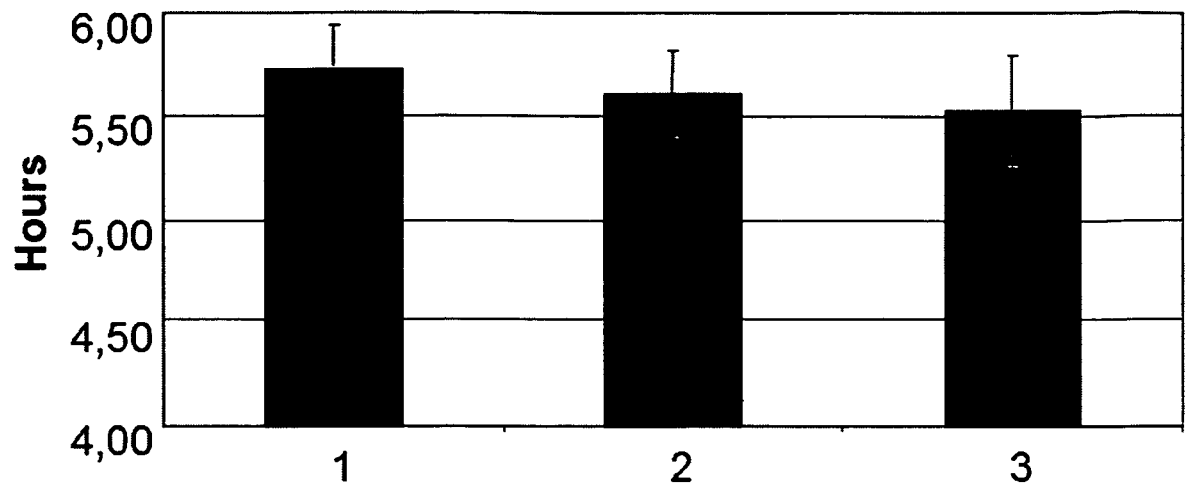
FIG. 1 depicts fermentation time for yoghurt (time to reach pH 4.55). Yoghurts were made with a lactic acid bacteria culture containing multiple strains of *Streptococcus thermophilus* and *Lactobacillus bulgaricus* containing 0% *Lactobacillus rhamnosus* CHCC12697 (1), 7.5% *Lactoba-* cillus rhamnosus CHCC12697 (2), and 15% *Lactobacillus rhamnosus* CHCC12697 (3). Standard deviation values are calculated from 3 replicates.

The inoculated solution was heated to 43° C. and fermented to pH 4.55. Time to reach pH 4.55 is the fermentation time which is shown in FIG. 1. When pH 4.55 was reached, the yoghurt was pumped through at post-treatment unit at 25° C. at a pressure of 2 bars and filled into plastic cups that were then put in cold storage. Rheological measurements were made after one day of cold storage. Evolution of the pH in the yoghurt was measured after 1, 14, 28 and 42 days of cold storage. Diacetyl measurements were made after 7 days of cold storage.

Example 3: Method for Measuring the Evolution of pH

On the day of analysis (after 1, 14, 28 and 42 days of cold storage) one plastic cup containing the yoghurt was taken out of the cold storage and pH was measured using a pH meter (pHM240, MeterLab). Prior to measurements, the pH meter was calibrated (2-point calibration with 7.00 and 4.01 buffers). As the samples, the buffers used for calibration were stored cold. FIG. 2 shows the evolution of pH.

Example 4: Method for Measuring Gel Firmness and Viscosity

Gel firmness was measured by the use of an Anton Paar rheometer with an automatic sample changer (Physica DSR Rheometer+ASC). The measuring bob was placed in the measuring cup containing 20 ml yoghurt sample, which had been stirred by hand and heated to 13° C. After the bob had been placed in the yoghurt sample a wait time was applied. By having a wait most of the structure broken by placing the bob in the cup was rebuild. Next, gel firmness was measured by oscillation. Here the strain was kept constant at 0.3% and the frequency was increased from 0.5 Hz to 30 Hz. From these measurements, the elastic modulus (G') and the viscous modulus (G") could be calculated, and from these the complex modulus (G*) was obtained:

$$G^* = \sqrt{G'^2 + G''^2}$$

G* at 1 Hz was then correlated to the gel firmness and used for comparison of the different samples (FIG. 3).

Using the same equipment (Anton Paar rheometer) the viscosity was measured by increasing the shear rate from 0.2707 1/s to 300 1/s with measuring points (shear stress) every 10 s. The shear rate was then decreased from 275 1/s to 0.2707 1/s with measuring points every 10 s. The viscosity of the product was correlated to the shear stress at 300 1/s in a flow curve measurement and depicted in FIG. 3.

Example 5: Method for Measuring Volatile Compounds (VOC)

The yoghurt samples were analyzed by static head space gas chromatography (HSGC) which is a powerful technique for analyzing volatiles in complex matrices. The setup consisted of a Static Head Space sampler connected to Gas Chromatograph with Flame Ionization Detector (FID). Below is a list of the apparatus (including column) and software used:

HS-autosampler: HS40XI, TurboMatrix 110, Perkin Elmer.
HS-software: HSControl v. 2.00, Perkin Elmer.
GC: Autosystem XL, Perkin Elmer.
GC-software: Turbochrom navigator, Perkin Elmer.
Column: HP-FFAP 25 m×0.20 mm×0.33 μm, Agilent Technologies Standards of known concentration were used to determine response factors (calibration), controls were used to control that the used response factors were stable within an analytical series as well as in-between series and over time (months). Concentration of volatiles (ppm) in samples and controls was determined using response factors coming from standards.

Samples were prepared by adding 200 µL of 4N $H_2SO_4$ to 1 g yoghurt sample.

The diacetyl content is depicted in FIG. 4.

Results

The graphs of FIGS. 1-4 summarize the results obtained in yoghurt made with lactic acid bacteria cultures with and without the *Lactobacillus rhamnosus* CHCC12697 strain.

The presence of the *Lactobacillus rhamnosus* CHCC12697 strain in the lactic acid bacteria culture used for making the yoghurt does not influence the fermentation time (FIG. 1), post acidification (FIG. 2) or the rheological characteristics of the yoghurt (FIG. 3).

When the *Lactobacillus rhamnosus* CHCC12697 strain is present in the lactic acid bacteria culture used for making the yoghurt significant higher amounts of diacetyl can be measured in the yoghurt (FIG. 4).

Example 6: Sensory Analysis of Yoghurt

In order to document the effect of the presence of *Lactobacillus rhamnosus* CHCC12697 in a yoghurt culture, a sensory evaluation of the creamy flavor was performed using a trained panel. The test was carried out as a 2-AFC test (AFC—alternative forced choice)/paired comparison test. This test is appropriate when two samples should be evaluated focusing on one attribute—in this case creamy flavor. This test should be considered as one-sided as the purpose was to confirm that the presence of the *Lactobacillus rhamnosus* CHCC12697 strain results in enhanced creamy flavor.

From a total of 20 servings, the assessors were asked to point out the sample (out of two) having the highest intensity of creamy flavor. The yoghurt containing the *Lactobacillus. rhamnosus* CHCC12697 strain was pointed out in 15 of 20 servings as having highest intensity of creamy flavor. This number constitutes a significant difference ($\alpha=0.05$).

Reference for 2-AFC test (AFC—alternative forced choice)/paired comparison test: Meilgaard M. C., Civille, G. V. & Carr, B. T. (2007). Sensory Evaluation Techniques, 4th Ed. Chapter 7: Attribute Difference Tests: How does attribute X Differ Between Samples? pp. 105-128. CRC Press Example 7: Screening of Selected VOC Relevant to Yoghurt Taste Produced by Two *Lactobacillus rhamnosus* Strains To determine the effect on levels of VOC relevant to yoghurt taste by use of *Lactobacillus rhamnosus* CHCC12697 and *Lactobacillus rhamnosus* CHCC12534, respectively, in fermented milk products tests were carried out at yoghurt fermentation conditions (43° C.) in milk (0.1% fat, 3.7% protein and 4.8% lactose) where the strains were tested alone or with (30% of inoculum) yoghurt cultures (*Lactobacillus bulgaricus* and *Streptococcus thermophilus*) as background. Levels of acetoin, acetaldehyde, ethanol and diacetyl were determined after 16 hrs of fermentation as described in Example 5.

The tests were performed in Microtiter plates using milk (0.1% fat, 3.7% protein and 4.8% lactose) and overnight cultures of *Lactobacillus rhamnosus* CHCC12697 and *Lactobacillus rhamnosus* CHCC12534 (10 g/l). Liquid handling was done by Multiprobe II PLUS robot (Perkin Elmer).

Results:

TABLE 1

Levels of VOC in milk fermented with CHCC12534, CHCC12697 or a yoghurt culture (Background).

|  | Acetaldehyde | Ethanol | Diacetyl | Acetoin |
|---|---|---|---|---|
| CHCC12534 (0.003 g/l) | 2.8 | 2.4 | 2.7 | 60.5 |
| CHCC12697 (0.003 g/l) | 3.7 | 1.9 | 2.8 | 67.4 |
| Background (0.007 g/l) | 5.8 | 1.8 | 1.8 | 36.5 |
| Milk | 0.1 | 0.3 | 0.0 | 0.0 |

Both CHCC12697 and CHCC12534 produce significantly higher levels of diacetyl and acetoin than the yoghurt culture used as background even at less than half the inoculation ratio. The yoghurt culture produce significantly higher acetaldehyde levels (higher inoculation ratio). The profiles of CHCC12697 and CHCC12534 are not significantly different to each other at single strain level (Table 1 and FIG. 5).

TABLE 2

Levels of VOC in milk fermented with CHCC12534 and a yoghurt culture (CHCC12534 & Background), CHCC12697 and a yoghurt culture (CHCC12697 & Background), or a yoghurt culture (Background).

|  | Acetaldehyde | Ethanol | Diacetyl | Acetoin |
|---|---|---|---|---|
| CHCC12534 (0.003 g/l) & Background (0.007 g/l) | 3.7 | 2.4 | 5.0 | 61.8 |
| CHCC12697 (0.003 g/l) & Background (0.007 g/l) | 12.7 | 4.2 | 5.2 | 127.9 |
| Background (0.007 g/l) | 5.8 | 1.8 | 1.8 | 36.5 |
| Milk | 0.1 | 0.3 | 0.0 | 0.0 |

CHCC12697 (30% of inoculum) with a yoghurt background culture produces significantly higher levels of acetoin, acetaldehyde and ethanol compared to CHCC12534 (30% of inoculum) with a yoghurt background and compared to background cultures alone.

CHCC12697 and CHCC12534 (both as 30% of inoculum) with a yoghurt background culture does not produce significantly different levels of diacetyl (Table 2 and FIG. 6).

Addition of 30% of CHCC12697 in a yoghurt culture resulted in an increase of VOC according to Table 3.

TABLE 3

Increase of VOC in a yoghurt culture with addition of 30% CHCC12697 or 30% CHCC12534

|  | CHCC12697 | CHCC12534 |
|---|---|---|
| Acetaldehyde | 119% | −36% |
| Ethanol | 133% | 33% |
| Diacetyl | 189% | 178% |
| Acetoin | 246% | 68% |

Example 8: Sensory Properties of Yoghurt with *Lactobacillus rhamnosus* CHCC12697

To analyze the gel firmness, mouth thickness and creamy flavor of yoghurt with *Lactobacillus rhamnosus* CHCC12697, yoghurt was made in 3 L scale containers from homogenized skim milk with 2% skim milk powder added. The base was pasteurized at 92° C. for 20 minutes and cooled down at 43° C. for inoculation. A background starter culture (*Streptococcus thermophilus* and *Lactobacil-* lus bulgaricus) was inoculated at 0.02%. *Lactobacillus rhamnosus* CHCC12697 was added as an overnight culture (15 g per batch).

Yoghurts were fermented to pH 4.55 then stirred, cooled and packed in 200 ml containers. Sensory evaluation of the sample was made 7 days after by a 5 member sensory panel. The panel used the reference sample (no flavor culture added) to create fixed points (value 0) for a rank order of the samples. The sample was then valued compared to the reference sample (−2 to 5) for each descriptor and average values for all judges were used to generate average value scores for each descriptor (Table 4).

TABLE 4

Sensory evaluation of yoghurt sample with *Lactobacillus rhamnosus* CHCC12697 added.

| | Gel firmness | Mouth thickness | Creamy flavour | Acetaldehyde | Diacetyl |
|---|---|---|---|---|---|
| CHCC12697 (*Lb. rhamnosus*) | 2 | 1.8 | 1.5 | 0.8 | 1.8 |
| Background/ No flavor | 0.1 | 0.5 | 1 | 0.1 | 0.25 |

Addition of CHCC12697 to the yoghurt results in high gel firmness, good mouth thickness and an enhanced creamy flavor.

Example 9: Method for Gouda40+ Cheese Make

Gouda40+ cheese was made from 150 L of pasteurized whole milk (72° C. for 20 sec). The milk was cooled to 5° C. and it was standardized according to the protein level (3.4 to 3.7%) with 38% cream prior to use (fat-to-protein ratio). The standardization was calculated based on the protein content of the milk and targeting a Gouda cheese with 40% fat in dry matter.

After standardization the milk was preheated in a heat-exchanger to the pre-ripening temperature of 32° C. and pumped to the cheese vats. A slow agitation (235 rpm) was continued until rennet was dispersed in the milk.

The Gouda40+ cheese was made using the parameters in Table 5.

An addition of 0.01% (w/w) acidifying culture (CHN-19, Chr. Hansen A/S), 0.02% (w/w) rennet (Chy-Max Plus, Chr.Hansen A/S), 0.01% (w/w) CaCl$_2$ (34% solution) and 0.01% (w/w) nitric acid was added to each cheese vat. A 0.02% (w/w) of adjunct culture (*Lactobacillus rhamnosus* CHCC12697) was added to one vat in order to test the effect of the strain on diacetyl odor and flavor after 7 weeks of ripening.

Cheeses were salted for 20 hrs in 22% brine at 10° C. Cheeses were coated and vacuum packed in plastic bags and stored at 9° C. for 1 week followed by 3 weeks at 13° C. and 2 weeks at 9° C. Hereafter the Gouda40+ was stored at 5° C.

TABLE 5

Cheese make parameters for Gouda40+.

| Step | Duration | Value |
|---|---|---|
| Pre-fermentation | 35 min | 32° C. |
| Rennet time | 35 min | |
| Pre-stirring | 20 min | |

TABLE 5-continued

Cheese make parameters for Gouda40+.

| Step | Duration | Value |
|---|---|---|
| Whey off | 5 min | 52.5 kg |
| Middle stirring | 10 min | |
| Scald time | 15 min | 38° C./45 kg water at 51° C. |
| Final stirring | 40 min | |
| Curd to end of vat | 5 min | |
| Pre-pressing | 25 min | 1 bar/10 min-2 bar/15 min |
| Pressing 1 | 15 min | 2 bar/15 min |
| Pressing 2 | 15 min | 3.5 bar/15 min |
| Pressing 3 | 90 min | 5 bar/90 min |

Example 10: Chemical Analysis of Cheese

In order to document the effect of the presence of *Lactobacillus rhamnosus* CHCC12697 in a Gouda40+ cheese, a sensory evaluation of the diacetyl odor and flavor, respectively, was performed using a trained panel.

The sensory evaluation was carried out using a ranking test. The samples were kept at 13° C. prior to the sensory evaluation. Samples were served randomly in plastic boxes with a lid and labelled with a three-digit random number. The cheese samples were scored at a scale going from 1-8, one being low intensity odor or flavor and eight being high intensity odor or flavor. A variance analysis was carried out for each of the sensory descriptors. The results of the ANOVA were explained by means of a plot showing the average value of the sensory descriptor as assed by 12 assessors. The plots also showed an interval around each average. The intervals displayed were based on Fisher's least significant difference (LSD) procedure. They were constructed in such a way that if two averages are the same, their intervals will overlap 95.0% of the time. Any pair of intervals that does not overlap vertically indicates a pair of averages with statistically significant difference.

Addition of *Lactobacillus rhamnosus* CHCC12697 to the Gouda40+ cheese significantly increased the sensory perception of diacetyl odor and flavor (FIGS. 7 and 8).

Example 11: Chemical Analysis of Cheese

In order to document the effect of the presence of *Lactobacillus rhamnosus* CHCC12697 in a Gouda40+ cheese, a chemical analysis of the diacetyl content was performed using gas chromatography as described in Example 5 except for the sample preparation of cheese.

Cheese plugs were sampled using a disposable 3 mL syringe. The bottom is removed with a knife, and the syringe is pushed into the cheese, cutting out a "plug". The "plug" was transferred to 20 mL head space vial. For analysis of oxygen sensitive compounds, the vial was flushed with nitrogen prior to closure with cap. No acid was added to cheese samples.

Addition of *Lactobacillus rhamnosus* CHCC12697 to the Gouda40+ cheese significantly increased the level of diacetyl in the cheese (FIG. 9).

Deposits and Expert Solution

The applicant requests that a sample of the deposited micro-organisms stated below may only be made available to an expert, until the date on which the patent is granted.

The *Lactobacillus rhamnosus* strain CHCC12697 was deposited on Mar. 1, 2011, at the German Collection of Microorganisms and Cell Cultures (Deutsche Sammlung von Mikroorganismen und Zellkulturen GmbH; DSMZ), Inhoffenstr. 7B, D-38124 Braunschweig and given Accession No. DSM 24616. The *Lactobacillus rhamnosus* strain CHCC12534 was deposited on Jun. 12, 2019 at the DSMZ, and given Accession No. DSM 33157. The deposits were made under the terms of the Budapest Treaty on the international recognition of the deposit of microorganisms for the purposes of patent procedure.

REFERENCES

Jyoti, B. D., Suresh, A. K., and Venkatesh, K. V. (2003): Diacetyl production and growth of *Lactobacillus rhamnosus* on multiple substrates. World Journal of Microbiology & Biotechnology 19: 509-514.
U.S. Pat. No. 4,678,673 (Marshall et al.)
U.S. Pat. No. 4,867,992 (Boniello et al.)
U.S. Pat. No. 5,236,833 (Duboff et al.)

The invention claimed is:

1. A method for preparing a dairy product comprising inoculating a milk substrate with a starter culture and *Lactobacillus rhamnosus* strain CHCC12697 (DSM 24616) or a mutant thereof, wherein the mutant strain is derived from CHCC12697 and leads to the same or increased diacetyl levels and the same or increased acetoin levels as the CHCC12697 strain when used to prepare a dairy product via comparable methods, and wherein the *Lactobacillus rhamnosus* strain or mutant thereof leads to increased levels of acetoin, as compared to *Lactobacillus rhamnosus* strain CHCC12534 (DSM 33157), when inoculated into a milk substrate with a starter culture comprising *Lactobacillus bulgaricus* and *Streptococcus thermophilus*.

2. The method of claim 1, wherein the dairy product prepared by the method is a fermented milk product.

3. The method of claim 2, wherein the fermented milk product is a yoghurt.

4. The method of claim 1, wherein the dairy product prepared by the method is a cheese.

5. The method of claim 1, wherein the dairy product prepared by the method comprises at least 0.75 ppm of diacetyl.

6. The method of claim 5, wherein the dairy product prepared by the method comprises at least 1.5 ppm of diacetyl.

7. The method of claim 1, wherein the method for preparing the dairy product further comprises fermenting the milk substrate.

8. The method according to claim 7, wherein the fermenting is at a temperature above 35° C.

9. The method of claim 1, wherein the starter culture of the method for preparing the dairy product is a thermophilic starter culture.

10. The method of claim 1, wherein the starter culture of the method for preparing the dairy product comprises one or more bacterium from a genus independently selected from the group consisting of *Lactococcus, Streptococcus* and *Lactobacillus*.

11. The method of claim 1, wherein the method for preparing the dairy product comprises inoculating the milk substrate with the *Lactobacillus rhamnosus* strain CHCC12697 (DSM 24616).

12. The method of claim 1, wherein the dairy product prepared by the method has an increased diacetyl flavor and odor relative to a dairy product produced by a comparable method but without inoculating a milk substrate with the *Lactobacillus rhamnosus* strain CHCC12697 (DSM 24616) or the mutant thereof.

13. The method of claim 1, wherein, in the method for preparing the dairy product, the *Lactobacillus rhamnosus* strain CHCC12697 (DSM 24616) does not significantly affect the rheology or post-acidification of the prepared dairy product.

14. The method of claim 1, wherein the mutant is obtained by a method that comprises exposing a *Lactobacillus rhamnosus* strain CHCC12697 (DSM 24616) to radiation, UV light, and/or chemical treatment.

* * * * *